United States Patent [19]

Thomas

[11] Patent Number: 4,865,594
[45] Date of Patent: Sep. 12, 1989

[54] ABSORBENT PAD FOR OSTOMY APPLIANCE

[75] Inventor: Tom G. Thomas, Columbus, Ohio

[73] Assignee: Thomas Medical, Columbus, Ohio

[21] Appl. No.: 170,260

[22] Filed: Mar. 18, 1988

[51] Int. Cl.⁴ .............................................. A61F 5/44
[52] U.S. Cl. ..................................... 604/332; 604/389
[58] Field of Search ........................... 604/332–345, 604/358, 365, 366, 377, 385.1, 385.2, 386, 389, 387, 393, 401, 402

[56] References Cited

U.S. PATENT DOCUMENTS

| | | | |
|---|---|---|---|
| 2,205,270 | 6/1940 | Perry | 604/337 |
| 2,520,831 | 8/1950 | Chincholl | 604/335 |
| 2,618,265 | 11/1952 | Adams et al. | 604/402 |
| 3,556,096 | 1/1971 | Fuller et al. | 128/157 |
| 3,773,048 | 11/1973 | Kirkliauskas | 604/345 |
| 3,895,629 | 7/1975 | Snyder | 128/DIG. 26 |
| 4,085,752 | 4/1978 | Canale | 604/377 |
| 4,519,798 | 5/1985 | Dinius | 604/358 |
| 4,561,858 | 12/1985 | Allen, Jr. et al. | 604/332 |
| 4,615,696 | 10/1986 | Jackson et al. | 604/389 |

FOREIGN PATENT DOCUMENTS 1030033  4/1978  Canada ............................... 604/337

Primary Examiner—C. Fred Rosenbaum
Assistant Examiner—Mario Costantino
Attorney, Agent, or Firm—George Wolken, Jr.

[57] ABSTRACT

The present invention describes a fluid absorbing pad for use with a typical ostomy appliance, specially suited for absorbing various body fluids external to the ostomy bag. This device absorbs perspiration, as well as acidic waste fluids as they may leak through an imperfect joint between a typical ostomy bag and adhesive wafer near the end of the useful service life of the ostomy appliance. The present invention increases the comfort of the ostomy patient in the wearing of the typical ostomy appliance, especially when used in combination with an ostomy belt. The present invention also extends the useful life of each ostomy appliance.

3 Claims, 1 Drawing Sheet

ABSORBENT PAD FOR OSTOMY APPLIANCE

BACKGROUND OF INVENTION

This invention relates to a medical-surgical apparatus and its method of use. More particularly, this invention relates to a pad specially suited for use with ostomy appliances and constructed so as to absorb various body fluids external to the ostomy bag, reducing thereby patient discomfort and extending the useful service life of each ostomy appliance.

There exist several intestinal or urinary diseases which are best treated, according to the currently preferred medical procedures, by surgical rerouting of wastes from the patient's usual waste elimination route, through an artificial opening surgically constructed in the abdominal wall. Among the more common types of such surgical procedures are colostomy, ileostomy and urostomy. Colostomy is the surgical construction of an artificial opening through the abdominal wall to the large intestine, thus bypassing the colon. This surgery allows waste material usually exiting from the body via the colon to exit via this artificial opening. The artificial opening thereby constructed in the abdominal wall is called the stoma. Typically a small tubular protrusion (1-3 cm) external to the body is allowed by the surgeon to permit easier collection of waste materials exiting from the body through the stoma. Similar artificial openings through the abdominal wall to the bladder, bypassing the ureter, is known as a urostomy. An ileostomy typically results in the removal of the large intestine and rectum, surgically creating an opening directly to the ileum.

For many of the common ostomy procedures, the patient loses voluntary control over his elimination functions. Therefore, an appliance must be worn at all times to insure collection of eliminated waste materials as they exit the body through the stoma, no longer under the conscious control of the patient.

The typical such ostomy appliance consists essentially of a collection bag firmly attached to the skin of the patient by means a suitable adhesive, occasionally supplemented by means of an ostomy belt to help keep the ostomy appliance firmly in position. Since 24 hour per day collection is frequently required, patient comfort, skin irritation, minimal interference with physical activities and appearance of the patient are all important considerations in the design and use of an ostomy appliance.

Typically, the useful service life of an ostomy appliance will be 1-4 days depending on many factors. Some of these factors include the level of activity of the patient, the climate and weather, the nature of the perspiration generated by the patient, the nature, acidity and quantity of the waste products expelled, and of course the design, construction and use of the ostomy appliance. Use and frequent replacement of such ostomy appliances are continuous requirements in the life of an ostomy patient. Therefore, the cost of the appliance itself becomes a significant consideration in the lifetime treatment of ostomy patients. It is a major goal of the present invention to add to the useful life of each ostomy appliance while, at the same time, increasing the comfort of the patient.

SUMMARY AND OBJECTS OF INVENTION

The present invention discloses an absorbent pad of a design suited for use with typical ostomy appliances and suited for adsorption of perspiration, fluid wastes and other materials tending to increase patient discomfort and shorten the useful service life of the ostomy appliance.

A primary object of the present invention is to provide a device for the absorption of fluids from the region where a typical ostomy appliance is attached to the skin of a patient.

Another major object of the present invention is to add to the comfort of the patient in the use of typical ostomy appliances by reducing the contact of the patient with irritating fluids and provide a cushion between the patient and the typically rigid ostomy belt ring.

A further object of the present invention is to absorb perspiration from the region of adhesive used in joining an ostomy appliance to the patient's skin.

Yet another object of the present invention is to absorb body waste fluids, intended to be collected by the ostomy bag, which occasionally seep through the joint of the typical ostomy bag with the skin-adhesive device.

Another object of the present invention is to add to the useful service life of a typical ostomy appliance.

DESCRIPTION OF PREFERRED EMBODIMENTS

Figure 1:
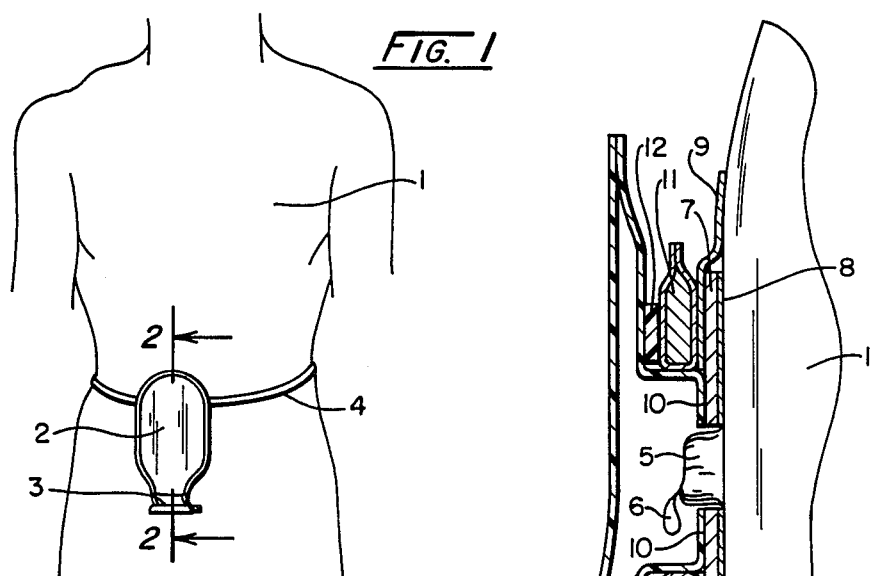
FIG. 1. Perspective view of a typical ostomy appliance as worn with an ostomy belt by a typical patient.

FIG. 1 shows in perspective view an ostomy patient, 1, as a typical ostomy appliance would be used by such a patient. The ostomy bag, 2, would be attached to the skin of the patient and, typically, have a closure device, 3, which permits the contents of the bag, 2, to be emptied without requiring replacement of the entire ostomy bag. Also shown in FIG. 1 is a typical ostomy belt, 4. The purpose of an ostomy belt is to provide additional security in holding the ostomy appliance in position over the stoma. However, its use is not required and many ostomy patients frequently dispense with the ostomy belt. It is included and discussed along with the present invention under the understanding that it is an optional device. The present invention can quite easily be used with or without the ostomy belt and provides benefits to the patient in either case. Use of the present invention with and without the ostomy belt will be described concurrently, with the understanding that the patient has the option of the ostomy belt or not.

Figure 2:
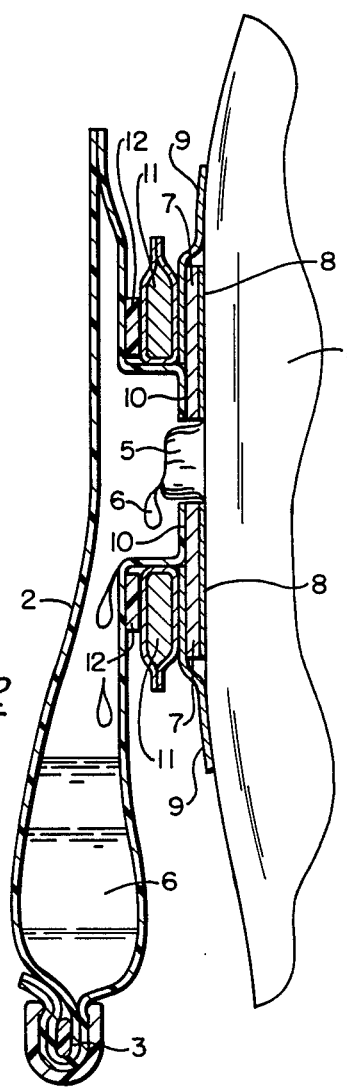
FIG. 2. Cross-sectional view through ¢2" showing the use of the present invention and as it would be used with a typical ostomy belt and ostomy belt ring.

FIG. 2 shows in cross-sectional view taken along axis 2—2 the detailed attachment means for the typical ostomy appliance to the patient, including the use of the present invention.

As described above, the patient, 1, in receiving the typical surgical procedure also receives a stoma, 5, through which waste material, 6, exits from the body of the patient. This waste material, 6, collects at the bottom of ostomy bag, 2, from which it can typically be removed by releasing a clip, 3, thereby unsealing an opening in the bag placed there specifically for the removal of waste, 6, from bag, 2.

The procedure whereby the ostomy appliance is attached to the skin of the patient is critical in the comfort of the patient and is the primary concern of the present invention. We describe here a typical mechanism for joining an ostomy appliance to the skin of the patient. Slight variations are well known to patients, and others skilled in the art of construction and use of such ostomy appliances. We will describe here a common type of ostomy appliance with the understanding that similar devices, obvious to persons having ordinary skills in the art, are well known. Such obvious and similar devices can also be used with the present invention as will be clear from the detailed description herein.

Typically, an annulus of relatively soft, rubberlike material, 7, known as an adhesive wafer is joined in the inner face, 10, to the ostomy bag, 2. This wafer 7, will commonly be made of an adhesive rubber or a soft plastic, and will be joined to ostomy bag 2 at location 10 by a heat seal or other common joining procedure. The adhesive nature of the wafer will provide suitable attachment to the patient in many cases. However, it may be desired by the patient to use an additional adhesive, 8 typically in a paste or powder form. The patient would typically apply such adhesive paste or powder for additional adhesion in the process of putting on a new ostomy appliance.

In typical ostomy appliances, the adhesive wafer, 7 is surrounded by a annular device, 9. Such structures may be made of a rigid material, although most such devices are presently made of a gas-permeable paper, commonly called "paper tape". Paper tape is made gas-permeable to decrease the probability of skin irritation to the patient. Such paper tape has additional adhesive on the side towards the patients skin, thus adding to the security of attachment of the ostomy appliance. In addition, the paper tape, 9 is typically made to be hypoallergenic to reduce the possibility of an adverse reaction from the patient. The paper tape is also typically made to be permeable to fluids.

Shown as 12 in FIG. 2 is the ring by which the ostomy belt, 4, secures the ostomy appliance in place. This ostomy belt ring, 12 is typically made of reasonably rigid plastic, typically polyethlyene, and is firmly secured to the ostomy belt, 4. The snug fit of the ostomy belt, 4, about the patient assists in keeping the ostomy bag, 2, at its proper location. As noted above, the use of the ostomy belt is optional and many ostomy patients do not utilize such a device.

The ostomy belt offers the patient certain advantages in increased security in holding the ostomy bag in place. However, disadvantages are also present. For example, the ostomy belt ring, 12, is typically made of rigid plastic. This increases the discomfort to the patient in sitting, or in certain physical activity. Mitigation of this discomfort caused by use of an ostomy belt ring is among the benefits of the present invention.

Another serious problem confronting the ostomy patient is seepage of fluid from inside the ostomy bag, 2, at the location, 10, of the joint with the adhesive wafer, 7. Since the ostomy belt ring, 12, is typically made of rigid plastic, there exists the possibility of the ostomy belt ring tearing into the ostomy bag itself, releasing large amounts of waste fluids. Such fluids are typically highly acidic, leading to serious irritation of the patient's skin when such leakage happens. The presence of an ostomy ring, places the additional strains on the joint, 10 by reason of causing increased tension on the ostomy bag, 2, which must be supported by the adhesive wafer, 9, through joint 10. With or without use of an ostomy ring, the normal motion of an active individual often causes leakage to occur at the location of the joint, 10. This is yet another problem for which the present invention provides a certain measure of relief for the patient.

The device which is the subject of the present invention is shown as 11 in FIG. 2. When the patient is using an ostomy belt and ostomy belt ring, the device comprising the present invention is placed between the ostomy belt ring and the paper tape, as shown in FIG. 2. Without the use of an ostomy belt, the present invention would likewise be positioned between the paper tape, 9 and the ostomy bag, 2.

Figure 3:
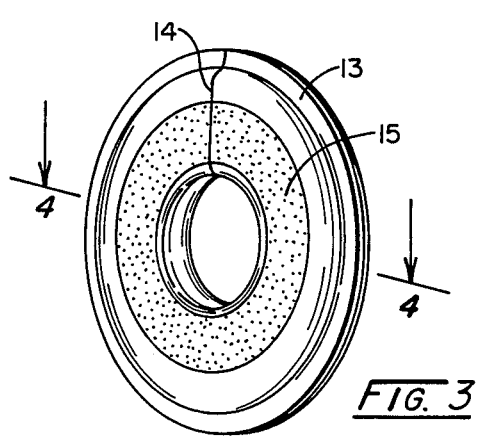
FIG. 3. Perspective view of the absorbent device subject of the present invention.
Figure 4:
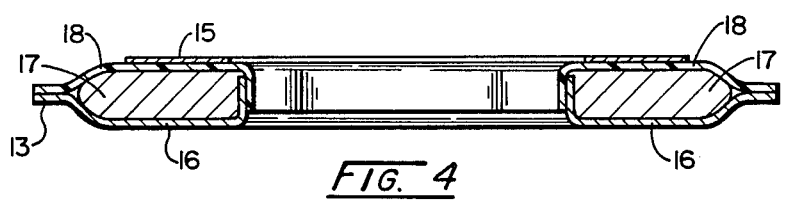
FIG. 4. Cross-sectional view of the absorbent device of the present invention through "4".

The detailed structure of the absorbent pad, 11, is shown in perspective view in FIG. 3 and in crosssection through axis 4—4 in FIG. 4.

The absorbent pad of the present invention consists in a typical embodiment of a annular-shaped ring of absorbent material, typically cotton, having a typical thickness of 0.3 cm to 1.5 cm. In a typical embodiment, the present invention would have an inner circumference of typically 6 cm to 9 cm and an outer circumference of typically 10 cm to 13 cm. The precise inner and outer circumference would be chosen by the patient for maximum comfort when used along with the particular ostomy appliance preferred by that particular patient. As there are many such ostomy appliances in common use, it is obvious that several different sizes and thicknesses of absorbent pads will be required.

The detailed structure of the absorbent pad of the present invention consists, in a typical embodiment, of several parts. The side of the pad positioned toward the patient, 16, is typically made of material permeable to fluids. Thus, any perspiration, leakage from joint 10, or other fluids will be absorbed by the absorbent material 17 on the interior of the pad and kept from the skin of the patient by a wicking effect, in analogy to the functioning of an infant's diaper. The opposite face, 18, of the absorbent pad will not permit the passage of fluids, thus keeping the inner surface of the ostomy bag relatively free of such fluids.

In a typical embodiment, the present invention will have an adhesive ring, 15, on the impermeable face, 18 which faces toward the ostomy bag, away from the skin of the patient. This adhesive layer will, typically, serve to keep the absorbent ring in position with respect to the ostomy bag, 2. However, the essential functions of the present invention will be substantially unchanged without the use of this adhesive region, 15.

It may be convenient, but not essential, for the present invention to have a cut, 14, joining the inner and outer edges of the pad. This cut, 14, would allow the present absorbent pad to be placed around the ostomy bag in the position shown in FIG. 2 without the requirement of removing the ostomy bag, or forcing the waste-containing portion of the ostomy bag through the interior opening of the absorbent pad. Such cut, 14, is not essential to the operation of the present invention and need not by used.

It is also thought convenient in a typical embodiment of the present invention for the absorbent pad, 11, to be constructed with a relatively thin lip, 13 surrounding the region of absorbent material, 17. This lip, 13 would provide additional surface to grip the absorbent pad while placing it into position.

This absorbent pad has shown several advantages in tests by the inventor, an ostomy patient himself. The absorbent pad reduces the irritation of the patient's skin caused by perspiration and, in the same way, tends to insulate the critical joint, 10, from a certain amount of chemical attack. In both cases, the comfort to the patient is increased. In the same way, the ostomy appliance can be used 25% to 50% longer by the patient between changes, thereby reducing the cost to the patient.

In addition, the absorbent pad of the present invention has such a location and configuration to reduce the effects of acid leakage from joint 10 when small leaks appear. The present invention thereby slows down the process of causing acid burns to the patient, a much appreciated result for the ostomy patient.

I claim:

1. An annular absorbent pad in combination with an ostomy appliance, wherein said ostomy appliance comprises a means for collecting body fluids secreted from a stoma, and further comprises a fluid-impermeable means for adhering said collecting means to said stoma, and wherein said absorbent pad is positioned between said adhering means and said collecting means, wherein said absorbent pad comprises;
   (a) an annulus of absorbent material having an inner circumference from 6 cm to 90 cm in length, an outer circumference from 10 cm to 13 cm in length and a thickness from 0.3 cm to 1.5 cm.
   (b) a first face of said annulus allowing the reasonably free passage liquid therethrough, and a second opposite face of said annulus being impermeable to liquid.
   (c) an annular strip of adhesive as an integral part of said second face of said annular absorbent pad.

2. The combination claimed in claim 1 further comprising a thin annular region surrounding said outer circumference of said annular absorbent pad, and integrally attached thereto.

3. The combination claimed in claim 1 further comprising a thin cut completely connecting said inner circumference with said outer circumference.

* * * * *